US010184893B2

(12) United States Patent
Santori et al.

(10) Patent No.: US 10,184,893 B2
(45) Date of Patent: Jan. 22, 2019

(54) HYPERSPECTRAL SCANNING

(71) Applicant: HEWLETT PACKARD ENTERPRISE DEVELOPMENT LP, Houston, TX (US)

(72) Inventors: Charles M Santori, Palo Alto, CA (US); James William Stasiak, Lebanon, OR (US); Garry Hinch, Corvallis, OR (US)

(73) Assignee: Hewlett Packard Enterprise Development LP, Houston, TX (US)

( * ) Notice: Subject to any disclaimer, the term of this patent is extended or adjusted under 35 U.S.C. 154(b) by 0 days.

(21) Appl. No.: 15/549,159

(22) PCT Filed: Feb. 27, 2015

(86) PCT No.: PCT/US2015/018194
§ 371 (c)(1),
(2) Date: Aug. 5, 2017

(87) PCT Pub. No.: WO2016/137520
PCT Pub. Date: Sep. 1, 2016

(65) Prior Publication Data
US 2018/0024062 A1 Jan. 25, 2018

(51) Int. Cl.
G06K 9/00 (2006.01)
G01N 21/64 (2006.01)
(Continued)

(52) U.S. Cl.
CPC ........ *G01N 21/6456* (2013.01); *G01J 3/2823* (2013.01); *G01N 21/255* (2013.01);
(Continued)

(58) Field of Classification Search
USPC ........ 382/100, 103, 106, 112–114, 135, 162, 382/165, 168, 173, 181, 190, 209, 216,
(Continued)

(56) References Cited

U.S. PATENT DOCUMENTS 6,831,688 B2 * 12/2004 Lareau ..................... G01J 3/02
348/272
7,149,366 B1 12/2006 Sun
(Continued)

OTHER PUBLICATIONS

Ellis, J. M. et al., "Exploring for Onshore Oil Seeps with Hyperspectral Imaging," (Web Page), Published in Oil and Gas Journal, Sep. 10, 2001, pp. 49-58, vol. 99, No. 37, available at http://www.cpnt.ru/userfiles/oilseeps OGJ 09 2001 Zamudio.pdf.
International Search Report & Written Opinion received in PCT Application No. PCT/US2015/018194, dated Nov. 19, 2015, 9 pages.
(Continued)

*Primary Examiner* — Seyed Azarian
(74) *Attorney, Agent, or Firm* — Hewlett Packard Enterprise Patent Development

(57) ABSTRACT

Examples relate to providing hyperspectral scanning of a surface. In some examples, motion capture data of unobstructed portions of the surface are captured, and spectral data of the surface are captured through a slit assembly and diffraction grating. The motion capture data are processed to determine a movement of a scanning device. At this stage, the spectral data are translated and rotated based on the movement of the scanning device to generate images that each correspond to a different color channel.

11 Claims, 3 Drawing Sheets

(51) Int. Cl.
*G01J 3/28* (2006.01)
*G01N 21/25* (2006.01)
*G01N 21/31* (2006.01)
*G06T 7/00* (2017.01)
*G07D 7/00* (2016.01)
*H04N 5/262* (2006.01)
*B42D 25/378* (2014.01)

(52) U.S. Cl.
CPC ........... *G01N 21/31* (2013.01); *G01N 21/643* (2013.01); *G01N 21/645* (2013.01); *G06T 7/0004* (2013.01); *G07D 7/00* (2013.01); *B42D 25/378* (2014.10); *G01N 2021/6423* (2013.01); *G01N 2201/0221* (2013.01); *G01N 2201/062* (2013.01); *G06T 2207/10024* (2013.01); *G06T 2207/30144* (2013.01)

(58) Field of Classification Search
USPC ............... 382/219, 232, 254, 260, 274, 276, 382/286–294, 312, 321; 348/77, 272, 348/239, 294, 333.01
See application file for complete search history.

(56) References Cited

U.S. PATENT DOCUMENTS

| | | |
|---|---|---|
| 8,913,241 B2 | 12/2014 | Bhatia et al. |
| 2003/0076492 A1 | 4/2003 | Bradbury et al. |
| 2003/0193589 A1* | 10/2003 | Lareau ............... G01J 3/02 348/294 |
| 2010/0053612 A1 | 3/2010 | Ou-Yang et al. |
| 2012/0274783 A1 | 11/2012 | Ko et al. |
| 2014/0022414 A1* | 1/2014 | Bhatia ............... G01J 3/021 348/239 |
| 2014/0354868 A1* | 12/2014 | Desmarais ......... H04N 5/23293 348/333.01 |
| 2015/0015692 A1* | 1/2015 | Smart ............... G01J 3/2823 348/77 |

OTHER PUBLICATIONS

Tack, N. et al., "A Compact, High-speed, and Low-cost Hyperspectral Imager," (Research Paper), Proceedings for SPIE 8266, Silicon Photonics VII, 82660Q, Feb. 9, 2012, http://proceedings.spiedigitallibrary.org/proceeding.aspx?articleid=1344986.

* cited by examiner

HYPERSPECTRAL SCANNING

BACKGROUND

Identity theft, counterfeiting, warranty fraud, and forgery are creating a world-wide crisis threatening individuals, corporations and governments. Easy access to high-resolution copiers and scanners, sophisticated image processing software and other digital tools have made detection and prevention of such activities challenging and costly. As mobile and smart devices become more capable and with the evolution of the "Internet of Things" ecosystem, wireless financial transactions and the exchange of private and personal information have become casual and commonplace. These trends have provided highly motivated and increasingly sophisticated criminals with new access points and opportunities for fraud and identity theft.

In response, innovative printing technologies that provide enhanced security have been developed. To address counterfeit and forgery in particular, specialty inks can be used that are difficult to copy but can be verified using specialized tools. At the forefront of security printing are techniques that combine complicated spatial patterns with unique spectral signatures using mixtures of fluorescent inks.

BRIEF DESCRIPTION OF THE DRAWINGS

The following detailed description references the drawings, wherein.

DETAILED DESCRIPTION

As discussed above, fluorescent ink printing technologies can be used to provide enhanced security. For example, complex spatial patterns can be generated by thermal inkjet printing that uses quantum-dot-based inks. However, most techniques (e.g., laboratory spectrometers, imaging systems, etc.) for verifying the unique spectral and spatial signatures are expensive.

Examples herein describe a hand-held scanner that acquires two-dimensional images with up to 40 distinct wavelength channels (i.e., colors). In these examples, light is collected through a specially designed slit and illumination assembly, where the light is dispersed by a diffraction grating film and analyzed using a camera (e.g., web camera). Motion tracking is used to determine the scanner's motion, which in turn is used to build spectral image data in real time.

In some examples, motion capture data of unobstructed portions of the surface are captured, and spectral data of the surface are captured through a slit assembly and diffraction grating. The motion capture data are processed to determine a movement of a scanning device. At this stage, the spectral data at the current slit position are translated and rotated based on the movement of the scanning device to generate a set of two-dimensional images that each correspond to a different color channel. Taken together, this set of two-dimensional images constitute a hyperspectral image.

Figure 1:
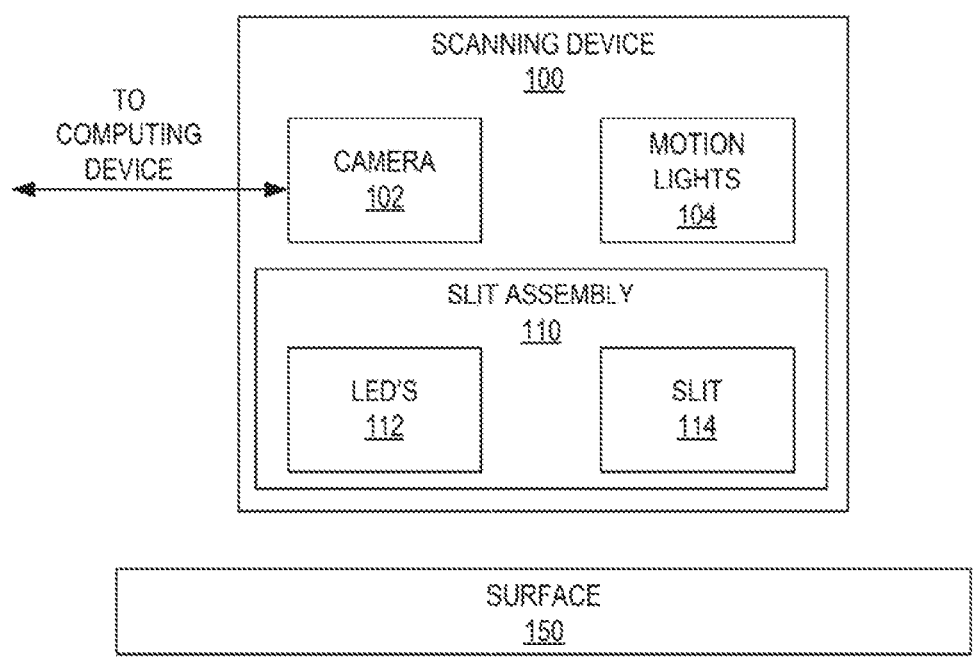
FIG. 1 is a block diagram of an example scanning device for providing hyperspectral scanning.

Referring now to the drawings, FIG. 1 is a block diagram of an example scanning device 100 for providing hyperspectral scanning. The example scanning device 100 includes a camera 102, motion lights 104, and a slit assembly 110, which further includes light-emitting diodes (LED's) 112 and a slit 114.

Camera 102 may be a web camera, a compact handheld camera, or other camera device that allows for hand-held mobility of scanning device 100 as described below. For example, camera 102 can be a web camera that is connected to a computing device via an interface such as a universal serial bus (USB) cable. In another example, camera 102 can be a smart phone camera, and the image processing can be performed by the smart phone. Camera 102 is configured to capture images of a field of view, which can vary depending on the lens and other components of camera 102. In scanning device 100, camera 102 is positioned to capture images as the scanning device 100 is moved over a surface 150. Surface 150 can include images printed using various inks (e.g., fluorescent ink) that are scanned by scanning device 100. Camera 102 can be configured with a diffraction grating (not shown) to capture spectral data from the slit assembly 110 as described below.

Motion lights 104 are configured to illuminate a portion of surface 150 that is used to obtain motion capture data for scanning device 100. Specifically, motion lights 104 are positioned to illuminate the portion of surface 150 that is unobstructed by the slit assembly 110. The unobstructed portion of the surface may include two or more unconnected regions, to allow for more accurate estimation of the rotation angle of the scanning device. For example, continuous stitching of a reference image of the portion of the surface 150 can be used by a motion-tracking algorithm to detect the motion of scanning device 100 as it is moved across surface 150. In some cases, motion lights 104 are compartmentalized (e.g., as shown in FIG. 2) to direct illumination toward the unobstructed portions of surface 150 and away from slit assembly 110.

Slit assembly 110 is positioned between camera 102 and surface 150 so that light from the LED's 112 is dispersed through the diffraction grating as spectral data. Typically, the slit will be positioned close (within a few millimeters) to the surface, while the diffraction grating will be positioned close to the camera lens. The underside of the slit assembly may be angled, allowing the LED's, positioned on either side of the slit, to illuminate the surface below the slit from an angle. LED's 112 may be ultraviolet LED's, white LED's, or any other LED's that can be used to generate spectral data. In some cases, slit assembly 110 can include multiple types of LED's 112, where each set of LED's 112 is used to perform a different type of spectroscopy (e.g., ultraviolet LED's for fluorescence spectroscopy, white LED's for reflection spectroscopy, etc.). The LED's 112 illuminate a portion of the surface that is generally larger than the slit, generating a combination of reflected, scattered and fluorescent light signals. The slit selects a portion of these light signals corresponding to a particular strip of the surface 150. A portion of this light reaches the diffraction grating, which generates a set of diffracted rays for which the ray angle depends on the wavelength of light. The camera lens then converts the wavelength-dependent angle to a wavelength-dependent position on the camera sensor. The data captured in a particular frame thus contains full spectral data for every point along the current position of the slit. This spectral data can then be added to the two-dimensional images (the hyperspectral data) through a geometric transformation (translation, rotation, and curvature correction) using parameters derived from the motion capture data by, for example, the computing device connected to camera 102.

Figure 2:
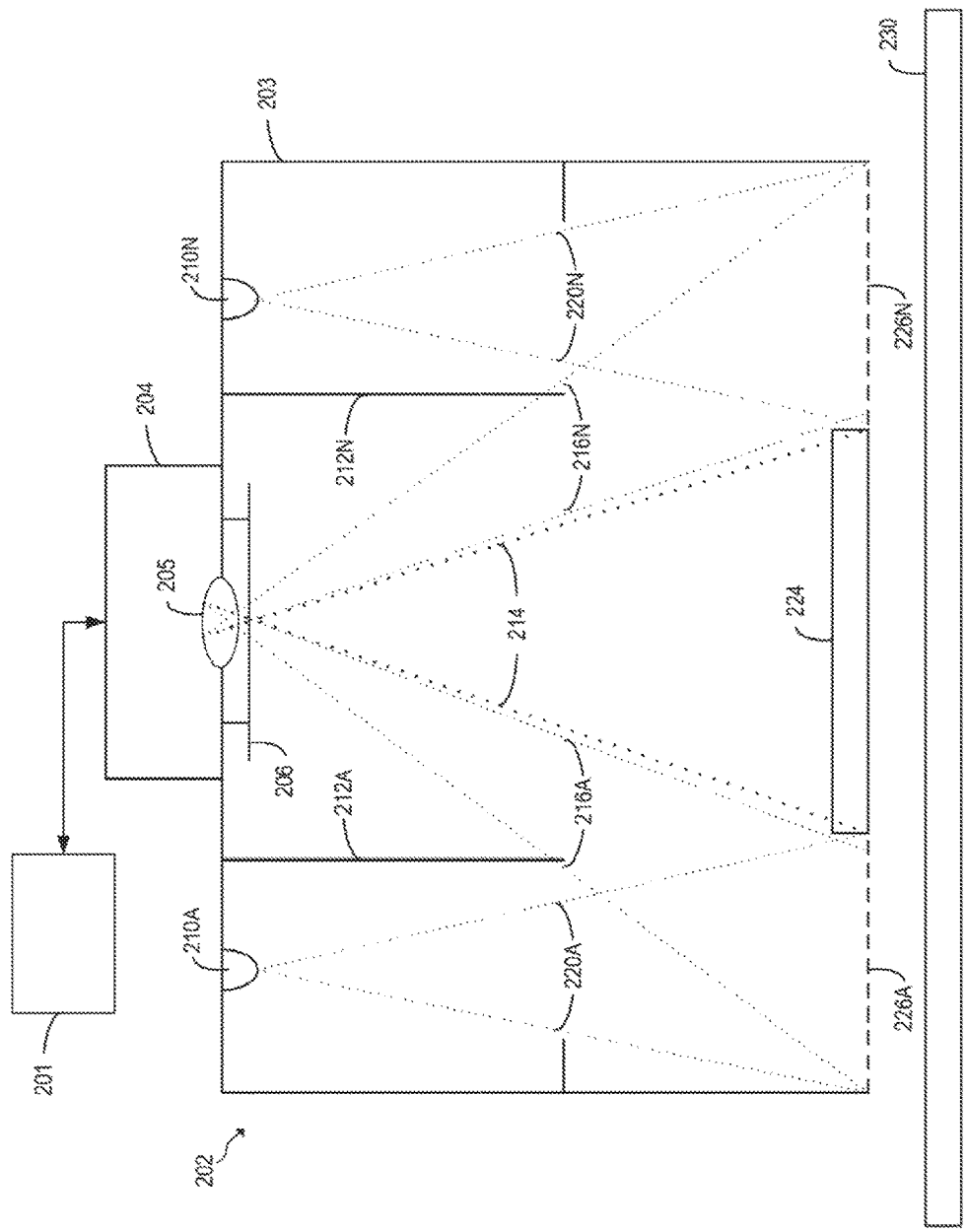
FIG. 2 is a block diagram of an example system including a computing device and a scanning device for providing hyperspectral scanning.

FIG. 2 is a block diagram of an example system including a computing device 201 and a scanning device 202 for providing hyperspectral scanning. The components of scanning device 202 may be similar to the corresponding components of scanning device 100 described with respect to FIG. 1.

Computing device 201 may include a non-transitory, computer-readable medium that stores code for providing hyperspectral scanning. The non-transitory, computer-readable medium may correspond to any typical storage device that stores computer-implemented instructions, such as programming code or the like. For example, the non-transitory, computer-readable medium may include one or more of a non-volatile memory, a volatile memory, and/or one or more storage devices. Examples of non-volatile memory include, but are not limited to, electrically erasable programmable read only memory (EEPROM) and read only memory (ROM). Examples of volatile memory include, but are not limited to, static random access memory (SRAM), and dynamic random access memory (DRAM). Examples of storage devices include, but are not limited to, hard disk drives, compact disc drives, digital versatile disc drives, optical drives, solid state drives and flash memory devices. Computing device 201 may also include a processor for retrieving and executing the instructions stored in the non-transitory, computer-readable medium to operate the computing device 201.

Scanning device 202 may include an enclosure 203 that prevents external light sources from interfering with the collection of spectral data. When the scanning device 202 is oriented for use above the surface 230, the camera 204 is installed at the top of the enclosure 203. The camera 204 is directed down through the enclosure 203 and towards a surface 230. The camera 204 includes a lens 205 that is used to capture images of the surface 230 as the scanning device 202 is repositioned. In this example, a printed image on the surface 230 can be scanned as the scanning device 202 is swept across the position of the printed image.

Diffraction grating 206 is positioned in front of lens 205 so that light 214 collected through slit assembly 224 can be captured by camera 204 as spectral data. Slit assembly 224 includes LED's (not shown) for directing LED light towards the surface. The LED illumination results in a combination of reflected, scattered and fluorescent light signals that are collected through a slit in slit assembly 224. Slit assembly 224 can include a variety of configurations of LED's. For example, slit assembly 224 can include ultraviolet LED's if spectral data is to be collected by fluorescence spectroscopy. In another example, slit assembly 224 can include white LED's if spectral data is to be collected by reflection spectroscopy. In yet another example, slit assembly 224 can include both ultraviolet and white LED's, where the mode of spectroscopy determines which set of LED's should be used during the scanning process.

Camera 204 is also configured to capture motion tracking data 216A, 216N for portions of the surface 230 that are unobstructed by the enclosure 203 or the slit assembly 224. The unobstructed portions of surface 230 are illuminated by motion lights 210A, 210N. Motion lights 210A, 210N may be light-emitting diodes. Motion lights 210A, 210N are also affixed to the top of enclosure 203, and in this example, are compartmentalized from the field of view of camera 204 by walls 212A, 212N. The compartments formed by walls 212A, 212N direct light 220A, 220N emitted from motion lights 210A, 210N towards the unobstructed portions of surface 230. The light 220A, 220N is reflected off the unobstructed portions and captured as motion tracking data 216A, 216N. For example, motion tracking data 216A, 216N may refer to continuous images of the unobstructed portions that can be stitched for motion tracking.

As spectral data and motion tracking data are collected by camera 204, the data can be transferred to computing device 201 for processing as described below with respect to FIG. 3. Alternatively, in other examples, camera 204 can include computing functionality for processing the data directly instead of using a separate computing device.

Figure 3:
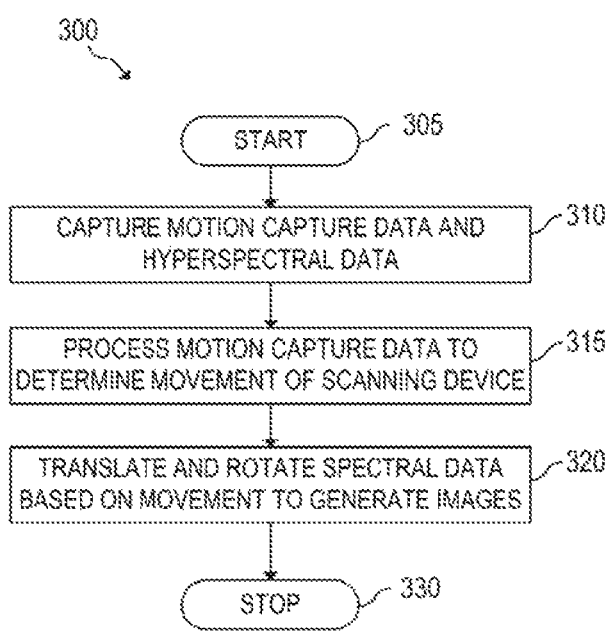
FIG. 3 is a flowchart of an example method for executing by a computing device to provide hyperspectral scanning.

FIG. 3 is a flowchart of an example method 300 for execution by a computing device 201 to provide hyperspectral scanning. Although execution of method 300 is described below with reference to computing device 201 of FIG. 2, other suitable devices for execution of method 300 may be used. Method 300 may be implemented in the form of executable instructions stored on a machine-readable storage medium and/or in the form of electronic circuitry.

Method 300 may start in block 305 and continue to block 310, where controller device 201 captures motion capture data and spectral data using a scanning device 202. For example, the data can be collected in real-time as the scanning device 202 is moved across a surface 230. In block 315, computing device 201 processes the motion capture data to determine a movement of the scanning device 202. For example, the motion capture data can be processed to determine the direction and velocity of the scanning device 201 as it is moved across the surface 230. As a further example, the translation vector between the current frame and a reference frame may be calculated by finding the maximum or centroid of the cross-correlation function calculated for the two images. The reference frame may be either the frame immediately preceding the current frame, or else it may be an image from the beginning of the data acquisition. The reference image may also be obtained by stitching together a set of images captured at different times. If the motion tracking region consists of two disconnected regions (such as 226A and 226N in FIG. 2), a separate translation vector can be computed for each region, and these two translation vectors can be combined to obtain a mean translation vector and a rotation angle.

In block 320, the spectral data along various color slices in the raw slit image is translated and rotated based on the movement of the scanning device 202, In block 325, the transformed spectral data are added to a number of two-dimensional images, where each image corresponds to a color channel. Taken together, this set of images constitutes a hyperspectral image in which a high-resolution spectrum exists at every spatial point in a two-dimensional array sampled from the surface 230. The composite hyperspectral image can be used, for example, to verify the integrity of a printed image (i.e., determine that verifiable inks were used to print the image), determine the color quality of a printed image, etc. Method 300 may subsequently proceed to block 330, where method 300 may stop.

The foregoing disclosure describes a number of examples for providing hyperspectral scanning. In this manner, the examples disclosed herein allow low-cost cameras to collect spectral data by using motion tracking to translate the spectral data collected through a slit assembly in real-time. Implementations of the examples can process frames (corresponding to a single slit position) at up to 30 frames per second using a standard processor in a laptop for the image processing. In such implementations, a hyperspectral data set of decent quality can be acquired in approximately 10 seconds.

We claim:

1. A system for providing hyperspectral scanning of a surface, comprising:
 a camera to obtain a video stream of the surface;
 a plurality of motion lights to illuminate unobstructed portions of the surface;
 a diffraction grating positioned between the camera and a slit assembly;
 the slit assembly including a plurality of light-emitting diodes (LED's) directed at the surface, the slit assembly proximate to the surface and positioned so that the diffraction grating disperses spectral data into the view of the camera; and
 a scanner to:
 process motion capture data of the unobstructed portions to determine a movement of the system;
 translate and rotate the spectral data based on the movement of the system to generate a plurality of two-dimensional images that each correspond to a different color channel; and
 use the plurality of two-dimensional images to verify a printed image on the surface.

2. The system of claim 1, wherein the plurality of LED's comprise a plurality of ultraviolet LED's and a plurality of white LED's, and wherein the plurality of ultraviolet LED's are used when the spectral data are captured via fluorescence spectroscopy, and wherein the plurality of white LED's are used when the spectral data are captured via reflection spectroscopy.

3. The system of claim 2, wherein the plurality of ultraviolet LED's are installed in a first half of the split assembly, and wherein the plurality of white LED's are installed in a second half of the split assembly, and wherein LED light from plurality of LED's reflects off the surface through a slit formed by the first half and the second half.

4. The system of claim 3, wherein the plurality of motion lights are compartmentalized so that light from the plurality of motion lights does not interfere with the LED light collected through the slit.

5. The system of claim 4, further comprising a plurality of walls to compartmentalize the plurality of motion lights from a field of view of the camera.

6. A method for providing hyperspectral scanning of a surface, comprising:
 capturing motion capture data of unobstructed portions of the surface using a camera;
 capturing spectral data of the surface via fluorescence spectroscopy through a slit assembly and diffraction grating, the slit assembly including a plurality of ultraviolet light-emitting diodes;
 processing the motion capture data to determine a movement of a scanning device; and
 translating and rotating the spectral data based on the movement of the scanning device to generate a plurality of two-dimensional images that each correspond to a different color channel.

7. The method of claim 6, further comprising using the plurality of two-dimensional images to verify a printed image on the surface.

8. The method of claim 6, further comprising using the plurality of two-dimensional images to determine a color quality of a printed image on the surface.

9. A non-transitory machine-readable storage medium encoded with instructions executable by a processor for providing hyperspectral scanning of a surface, the machine-readable storage medium comprising instructions to:
 capture motion capture data of unobstructed portions of the surface;
 capture spectral data of the surface through a slit assembly and diffraction grating, wherein the slit assembly includes a plurality of light-emitting diodes (LED's) for emitting LED light that is dispersed through the slit assembly into the diffraction grating as spectral data;
 process the motion capture data to determine a movement of a scanning device;
 translate and rotating the spectral data based on the movement of the scanning device to generate a plurality of two-dimensional images that each correspond to a different color channel; and
 use the plurality of two-dimensional images to verify a printed image on the surface.

10. The non-transitory machine-readable storage medium of claim 9, wherein the plurality of LED's are a plurality of ultraviolet LED's, and the spectral data are captured via fluorescence spectroscopy.

11. The non-transitory machine-readable storage medium of claim 9, wherein the plurality of LED's are a plurality of white LED's, and the spectral data are captured via reflection spectroscopy.

* * * * *